US010386234B2

(12) United States Patent
Gross

(10) Patent No.: US 10,386,234 B2
(45) Date of Patent: Aug. 20, 2019

(54) WIDEBAND SPECTROGRAPH

(71) Applicant: KLA-Tencor Corporation, Milpitas, CA (US)

(72) Inventor: Kenneth P. Gross, San Carlos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 96 days.

(21) Appl. No.: 15/485,097

(22) Filed: Apr. 11, 2017

(65) Prior Publication Data

US 2018/0216998 A1    Aug. 2, 2018

Related U.S. Application Data

(60) Provisional application No. 62/451,582, filed on Jan. 27, 2017.

(51) Int. Cl.
| | |
|---|---|
| *G01J 3/28* | (2006.01) |
| *G01J 1/42* | (2006.01) |
| *G01J 3/10* | (2006.01) |
| *G01J 3/02* | (2006.01) |
| *G01J 3/18* | (2006.01) |
| *G01J 3/36* | (2006.01) |
| *G01N 21/21* | (2006.01) |

(52) U.S. Cl.
CPC ............... *G01J 3/28* (2013.01); *G01J 1/429* (2013.01); *G01J 3/021* (2013.01); *G01J 3/0218* (2013.01); *G01J 3/108* (2013.01); *G01J 3/1804* (2013.01); *G01J 3/36* (2013.01); *G01N 21/211* (2013.01)

(58) Field of Classification Search
CPC .... G01J 3/108; G01J 1/429; G01J 3/28; G01J 3/0218; G01J 3/021; G01J 3/36; G01N 21/211
See application file for complete search history.

(56) References Cited

U.S. PATENT DOCUMENTS

| | | |
|---|---|---|
| 6,278,519 B1 | 8/2001 | Rosencwaig et al. |
| 6,744,505 B1 | 6/2004 | Wang et al. |
| 7,227,637 B2 | 6/2007 | Wang et al. |
| 7,399,975 B2 | 7/2008 | Harrison |

(Continued)

FOREIGN PATENT DOCUMENTS

| | | |
|---|---|---|
| CN | 204115867 U | 1/2015 |
| CN | 105549341 A | 5/2016 |

OTHER PUBLICATIONS

International Search Report and Written Opinion dated May 11, 2018 for PCT/US2018/015575.

*Primary Examiner* — David P Porta
*Assistant Examiner* — Fani Boosalis
(74) *Attorney, Agent, or Firm* — Suiter Swantz pc llo

(57) ABSTRACT

A wideband spectrograph apparatus includes a first spectrograph assembly and one or more subsequent spectrograph assemblies. Each subsequent spectrograph assembly is optically coupled to a previous spectrograph assembly and is configured to receive a cascading beam from one or more dispersion elements of the previous spectrograph assembly. The first spectrograph assembly is configured for detecting illumination in a first wavelength range and the one or more subsequent spectrograph assemblies are configured for detecting illumination in wavelength ranges different from the first or any previous wavelength ranges to provide simultaneous sampling of different spectral portions of an input beam.

33 Claims, 4 Drawing Sheets

(56) References Cited

U.S. PATENT DOCUMENTS

| | | |
|---|---|---|
| 7,633,625 B1 | 12/2009 | Woollam et al. |
| 7,764,376 B2 | 7/2010 | Fielden et al. |
| 7,869,040 B1 | 1/2011 | Kwak et al. |
| 8,119,991 B2 | 2/2012 | Harrison |
| 8,125,641 B2 | 2/2012 | Li |
| 8,148,900 B1 | 4/2012 | Kirk et al. |
| 9,160,137 B1 | 10/2015 | Abdolvand et al. |
| 2008/0204710 A1 | 8/2008 | Harrison et al. |
| 2009/0213377 A1 | 8/2009 | Scheiner et al. |
| 2013/0162982 A1 | 6/2013 | Miyazono |
| 2015/0049778 A1 | 2/2015 | Shchemelinin et al. |
| 2015/0300876 A1 | 10/2015 | Archer et al. |
| 2016/0161245 A1 | 6/2016 | Fu et al. |
| 2016/0202178 A1 | 7/2016 | Acosta et al. |

WIDEBAND SPECTROGRAPH

CROSS-REFERENCE TO RELATED APPLICATION

The present application claims the benefit under 35 U.S.C. § 119(e) of U.S. Provisional Application Ser. No. 62/451,582, filed Jan. 27, 2017, entitled ULTRA BROAD BAND SPECTROGRAPH COVERING VUV TO IR, naming Kenneth P. Gross as inventor, which is incorporated herein by reference in the entirety.

TECHNICAL FIELD

The present invention generally relates to a wide band spectrograph, and, more particularly, to a wide band spectrograph for analyzing light spanning vacuum ultraviolet light to infrared light.

BACKGROUND

As tolerances on process conditions in semiconductor device processing environments continue to narrow, the demand for improved process monitoring systems continues to increase. One monitoring approach includes spectroscopic analysis of spectral signatures, irradiance, and/or radiance over an extended wavelength range, such as deep UV (~100 nm) to mid IR (~10 µm) from a single light source beam. Current methods utilize multiple separate spectrograph units and sequential measurements to effectively cover such a broad spectral range. It would be desirable to provide a system to allow for very wide band spectrograph monitoring within a single simultaneous measurement time frame.

SUMMARY

A spectrograph apparatus is disclosed, in accordance with an illustrative embodiment of the present disclosure. In one embodiment, the apparatus includes a first spectrograph assembly. In another embodiment, apparatus includes a second spectrograph assembly optically coupled to the first spectrograph assembly and configured to receive a first cascading beam from one or more dispersion elements of the first spectrograph assembly. In another embodiment, the first spectrograph is configured for detecting illumination in a first wavelength range and the second spectrograph is configured for detecting illumination in a second wavelength range different from the first wavelength range. In another embodiment, the apparatus further includes a third spectrograph assembly optically coupled to the second spectrograph assembly and configured to receive a second cascading beam from one or more dispersion elements of the second spectrograph. In another embodiment, the third spectrograph is configured for detecting illumination in a third wavelength range different from the first wavelength and the second wavelength range.

A spectrograph apparatus is disclosed, in accordance with an illustrative embodiment of the present disclosure. In one embodiment, the apparatus includes a first spectrograph assembly. In another embodiment, the first spectrograph assembly includes one or more first dispersion elements for separating an input beam into a sampling beam and first cascading beam. In another embodiment, the apparatus includes one or more first detectors arranged to receive the sampling beam from the one or more dispersion elements. In another embodiment, the one or more first detectors are configured to detect illumination within a first wavelength. In another embodiment, a second spectrograph assembly is optically coupled to the first spectrograph assembly and configured to receive the first cascading beam from the one or more dispersion elements of the first spectrograph assembly. In another embodiment, the second spectrograph assembly includes one or more second dispersion elements for separating the first cascading beam from the first spectrograph assembly into a second sampling beam and a second cascading beam. In another embodiment, one or more second detectors are arranged to receive the second sampling beam from the one or more second dispersion elements. In another embodiment, the one or more second detectors are configured to detect illumination within a second wavelength range that is different from the first wavelength range.

A spectrograph apparatus for analyzing and recording spectral information is disclosed, in accordance with an additional and/or alternative embodiment of the present disclosure. In one embodiment, the apparatus includes a first spectrograph assembly. In another embodiment, the first spectrograph assembly includes one or more first dispersion elements for separating an input beam into a sampling beam and a cascading beam. In another embodiment, the one or more first detectors are arranged to receive the sampling beam from the one or more dispersion elements. In another embodiment, the one or more first detectors are configured to detect illumination within a first wavelength range. In another embodiment, a beam splitter is positioned within the cascading beam so as to split the cascading beam into a first component and a second component. In another embodiment, the apparatus includes a second spectrograph assembly. In another embodiment, the apparatus includes a second spectrograph assembly optically coupled to the first spectrograph assembly via the beam splitter. In another embodiment, the second spectrograph assembly is configured to receive the first component of the cascading beam from the one or more dispersion elements of the first spectrograph assembly. In another embodiment, the second spectrograph assembly includes one or more second dispersion elements for forming a second sampling beam. In another embodiment, the second spectrograph assembly includes one or more second detectors arranged to receive the second sampling beam from the one or more second dispersion elements. In another embodiment, the one or more second detectors are configured to detect illumination within a second wavelength range different from the first wavelength range. In another embodiment, the apparatus includes a third spectrograph assembly optically coupled to the first spectrograph assembly via the beam splitter. In another embodiment, the third spectrograph assembly is configured to receive the second component of the cascading beam from the one or more dispersion elements of the first spectrograph assembly. In another embodiment, the third spectrograph assembly includes one or more third dispersion elements for forming a third sampling beam. In another embodiment, the one or more third detectors are arranged to receive the third sampling beam from the one or more third dispersion elements. In another embodiment, the one or more third detectors are configured to detect illumination within a third wavelength range different from the first wavelength range and the second wavelength range.

A metrology system for analyzing and recording spectral information is disclosed, in accordance with an illustrative embodiment of the present disclosure. In one embodiment, the metrology system includes an illumination arm. In another embodiment, the metrology system includes a collection arm. In another embodiment, the system includes one or more spectrograph sub-systems. In another embodiment, the one or more spectrograph sub-systems comprise a first spectrograph assembly. In another embodiment, the one or more spectrograph sub-systems comprise a second spectrograph assembly optically coupled to the first spectrograph assembly and configured to receive a first cascading beam from one or more dispersion elements of the first spectrograph assembly, wherein the first spectrograph assembly is configured for detecting illumination in a first wavelength range and the second spectrograph assembly is configured for detecting illumination in a second wavelength range different from the first wavelength range. In another embodiment, the one or more spectrograph sub-systems further comprise a third spectrograph assembly optically coupled to the second spectrograph assembly and configured to receive a second cascading beam from one or more dispersion elements of the second spectrograph assembly, wherein the third spectrograph assembly is configured for detecting illumination in a third wavelength range different from the first wavelength and the second wavelength range.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

Referring generally to FIGS. 1A through 3, a wideband spectrograph is disclosed, in accordance with one or more embodiment of the present disclosure.

Embodiments of the present disclosure provide a wideband spectrograph for analyzing and recording spectral signatures, irradiance, and/or radiance over an extended wavelength range from the VUV (down to approximately 100 nm) up to the MID IR (up to approximately 10 µm), from a single light source beam or source FOV, and within a single temporal or time resolved integration period. One or more wideband spectrographs of the present disclosure may be incorporated within a semiconductor process control metrology tool. Such metrology tools may be used to measure structural and material characteristics, such as, but not limited to, material composition, dimensional characteristics of structures and films (e.g., film thickness and/or critical dimensions of structures, overlay, etc.) associated with various semiconductor fabrication processes/layers. In addition, the wideband spectrograph of the present disclosures provides for a broad class of absolute radiometric measurements over an extended wavelength range within a single simultaneous measurement time frame, enabling correlated and instantaneous (time resolved) spectral measurements.

The wideband spectrograph of the present disclosure includes a series of cascaded spectrograph assemblies. The series of the cascaded spectrograph assemblies provide for the simultaneous sampling of different spectral portions of an input beam to the wideband spectrograph. Each successive spectrograph assembly of the wideband spectrograph is optically cascaded relative to a previously spectrograph assembly, whereby the successive spectrograph receives a cascaded unused portion of an input beam from the previous spectrograph assembly.

Figure 1A:
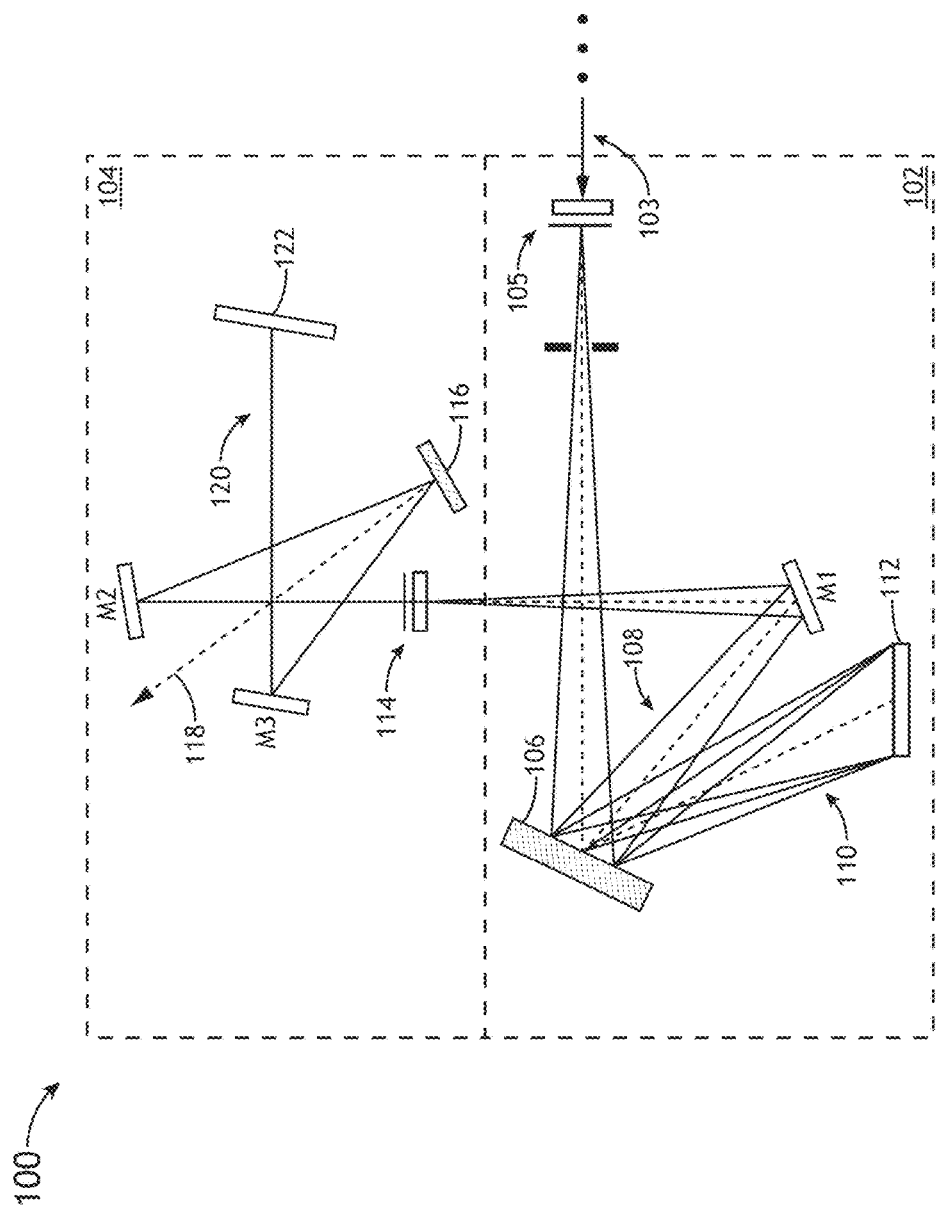
FIG. 1A illustrates a wideband spectrograph including two cascaded spectrograph assemblies, in accordance with one or more embodiments of the present disclosure.

FIG. 1A illustrates a wideband spectrograph 100 including two cascaded spectrograph assemblies, in accordance with one or more embodiments of the present disclosure.

In one embodiment, the wideband spectrograph 100 includes a first spectrograph assembly 102 and a second spectrograph assembly 104. In one embodiment, the second spectrograph assembly 104 is optically coupled to the first spectrograph assembly 102 so as to receive an output from first spectrograph assembly 102.

In one embodiment, the first spectrograph assembly 102 is configured for detecting illumination in a first wavelength range. In another embodiment, the second spectrograph assembly 104 is configured for detecting illumination in a second wavelength range. The first spectrograph assembly 102 and the second spectrograph assembly 104 may be configured such that the wavelength range detected by the second spectrograph assembly 104 is different from the wavelength range detected by the first spectrograph assembly 102 to allow for simultaneous measurement of multiple spectral ranges across an extended overall spectral range.

In one embodiment, the first spectrograph assembly 102 is configured for a spectral range including VUV light. For example, the first spectrograph assembly 102 may be configured for detecting light down to a range of 100-115 nm. For instance, the first spectrograph assembly 102 may be configured for detecting light having a wavelength between 115 and 300 nm. It is noted herein that the cut-off wavelength for $MgF_2$ windows is approximately 115 nm. In another embodiment, the second cascade spectrograph 104 is configured for detecting light in the spectral range of approximately 250 to 1100 nm. It is noted herein that the scope of the present disclosure is not limited to the wavelength ranges listed herein, which are provided merely for illustrative purposes. In another embodiment, the first spectrograph assembly 102 is purged with a selected purge gas (e.g., argon, nitrogen, and the like). In another embodiment, the first spectrograph assembly 102 is maintained in vacuum.

In one embodiment, the first spectrograph assembly 102 includes one or more first dispersion elements for separating an input beam 103 into a sampling beam 110 and a first cascading beam 108. The one or more first dispersion elements 106 may include any dispersion element known in the art, such as, but not limited to, a grating structure. For example, a first dispersion element 106 may include, but is not limited to, a diffraction grating.

In one embodiment, during operation, the first spectrograph assembly 102 receives an input beam 103. For example, the input beam 103 may include, but is not limited to, a light signal collected from a sample in response to a probe beam.

In another embodiment, at least a portion of the input beam 103 propagates through a first slit 105 to the first dispersion element 106. In another embodiment, the first dispersion element 106 separates the input beam 103 into the first sampling beam 110 and the first cascade beam 108. In another embodiment, the first sampling beam 110 is formed by one or more portions of diffracted light from the dispersion element 106. In another embodiment, the first detector 112 is positioned so as to receive the first sampling beam 110 from the first dispersion element 106. The first detector 112 may include any light detector device known in the art capable of detecting illumination within the first wavelength range. For example, the first detector 112 may include a light detector capable of detecting light within the spectral range of 115 to 300 nm. For instance, the first detector 112 may include, but is not limited to, one or more silicon-based charge coupled device (CCD) detectors.

In another embodiment, the first cascading beam 108 includes the 0th order beam from the first dispersion element 106. In this regard, the first dispersion element 106 may be arranged so as to reflect $0^{th}$ order light along a selected direction and on towards the second spectrograph assembly 104. For example, the first dispersion element 106 may be arranged to direct the first cascading beam (formed from $0^{th}$ order light) to mirror M1, which, in turn, reflects the first cascading beam 108 toward the second spectrograph assembly 104.

In one embodiment, the second spectrograph assembly 104 includes one or more second dispersion elements 116 for separating the first cascading beam 108 into a second sampling beam 120 and a second cascading beam 118. The one or more second dispersion elements 116 may include any dispersion element known in the art, such as, but not limited to, a grating structure. For example, a second dispersion element 116 may include, but is not limited to, a diffraction grating. In another embodiment, the second spectrograph assembly 104 is purged with a selected purge gas (e.g., argon, nitrogen and the like). In another embodiment, the second spectrograph assembly 104 is maintained in air.

In another embodiment, during operation, at least part of the first cascaded beam 108 propagates through slit 114. In turn, a second mirror M2 may direct the first cascaded beam 108 towards the second dispersion element 116.

In another embodiment, the second dispersion element 116 separates the first cascading beam 108 into the second sampling beam 120 and the second cascading beam 118. In another embodiment, the second sampling beam 120 is formed by one or more portions of diffracted light from the second dispersion element 116. In another embodiment, the second detector 122 is positioned so as to receive the second sampling beam 120 from the second dispersion element 116. For example, the second spectrograph assembly 104 may include mirror M3, which is arranged to receive diffracted light from the second dispersion element 116 and direct it to the second detector 122. The second detector 122 may include any light detector device known in the art capable of detecting illumination within the second wavelength range.

For example, the second detector 122 may include a light detector capable of detecting light within the spectral range of 250 to 1100 nm. For instance, the second detector 122 may include, but is not limited to, one or more silicon-based CCD detectors.

In another embodiment, the second cascading beam 118 is also formed with $0^{th}$ order light. It is noted that the second cascading beam 118 may be directed to a third spectrograph assembly (see FIG. 1B) or may be directed to a beam dump (not shown) if additional cascading of the input beam 103 is not necessary.

Figure 1B:
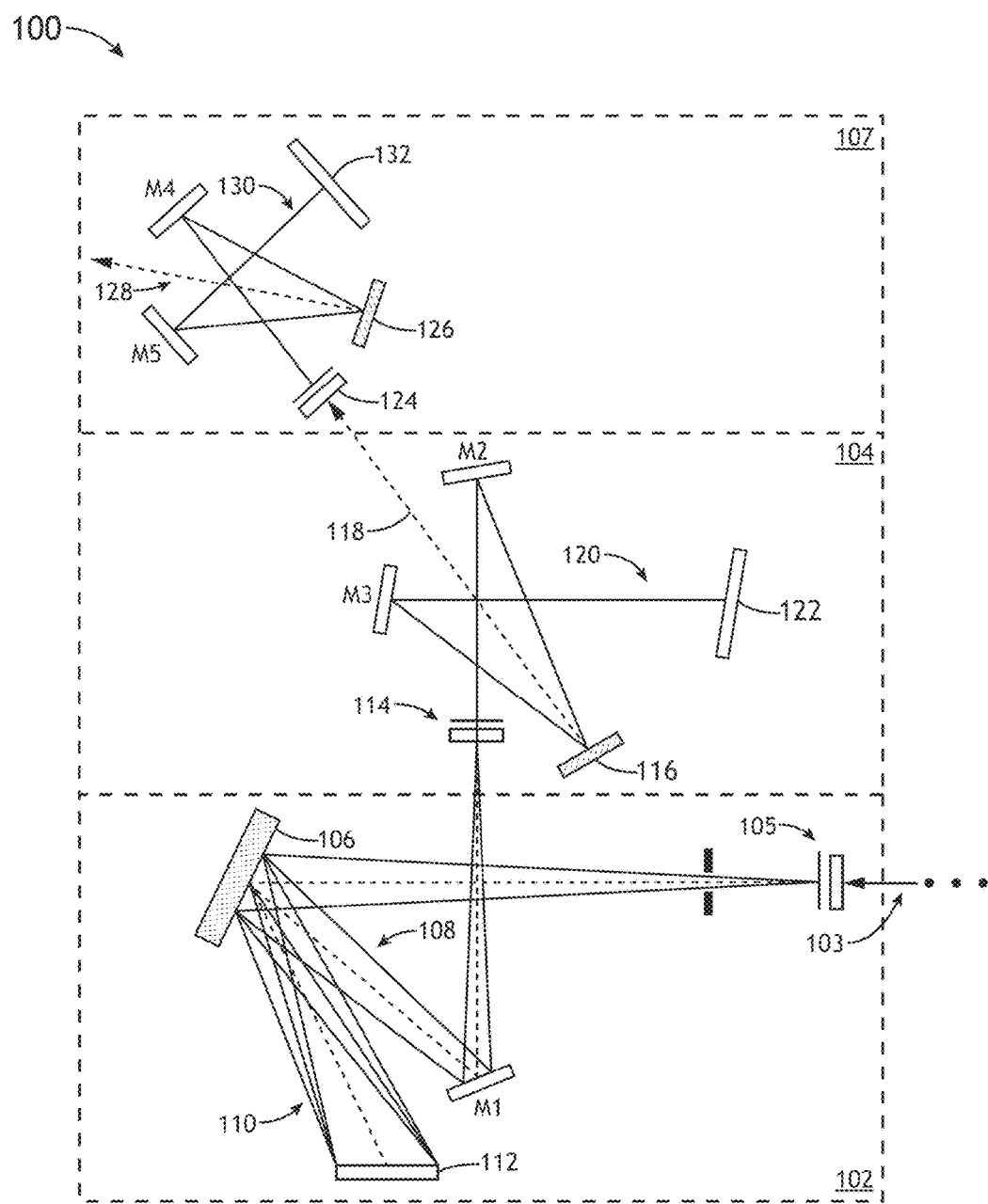
FIG. 1B illustrates a wideband spectrograph including three cascaded spectrograph assemblies, in accordance with one or more embodiments of the present disclosure.

FIG. 1B illustrates a wideband spectrograph 100 including three cascaded spectrograph assemblies, in accordance with one or more embodiments of the present disclosure.

It is noted that the various embodiments and configurations discussed previously herein with respect to FIG. 1A should be interpreted to extend to FIG. 1B unless otherwise noted.

In one embodiment, the wideband spectrograph 100 includes a third spectrograph assembly 107 configured for detecting illumination in a third wavelength range. In another embodiment, the third spectrograph assembly 107 is different from the wavelength ranges detected by the first spectrograph assembly 102 and the second spectrograph assembly 104 to allow for simultaneous measurement of multiple spectral ranges across an even more extended overall spectral range relative to the example in FIG. 1A. In another embodiment, the third spectrograph assembly 107 is purged with a selected purge gas (e.g., argon, nitrogen assembly, etc.). In another embodiment, the third spectrograph assembly 107 is maintained in air.

In one embodiment, the third spectrograph assembly 107 is optically coupled to the second spectrograph assembly 104. In this embodiment, the second cascading beam 118 is directed from the second dispersion element 116 of the second spectrograph assembly 104 to slit 124 of the third spectrograph assembly 107. In another embodiment, at least a portion of the second cascading beam 118 propagates through slit 124 to a fourth mirror M4. In another embodiment the fourth mirror M4 directs the second cascading beam 118 to a third dispersion element 126.

In another embodiment, the third dispersion element 126 separates the second cascading beam 118 into the third sampling beam 130 and the third cascading beam 128. In another embodiment, the third sampling beam 130 is formed by one or more portions of diffracted light from the third dispersion element 126. In another embodiment, the third detector 132 is positioned so as to receive the third sampling beam 130 from the third dispersion element 126. For example, the third spectrograph assembly 107 may include mirror M5, which is arranged to receive diffracted light from the third dispersion element 126 and direct it to the third detector 132.

The one or more third dispersion elements 126 may include any dispersion element known in the art, such as, but not limited to, a grating structure. For example, a third dispersion element 126 may include, but is not limited to, a diffraction grating.

The third detector 132 may include any light detector device known in the art capable of detecting illumination within the third wavelength range. For example, the third detector 132 may include a light detector capable of detecting light within the spectral range of 900 to 2500 nm. For instance, the third detector 132 may include, but is not limited to, one or more InGaAs-based CCD detectors.

It is noted that the use of the first, second and third spectrograph assemblies provides simultaneous measurement of three spectral ranges (e.g., 115-300 nm, 250-1100 nm and 900-2500 nm) to provide very wideband spectrographic capabilities. In addition, the implementation of the three spectrograph assemblies 102, 104 and 107 provides that four octaves of wavelength dynamic range may be realized.

Figure 2:
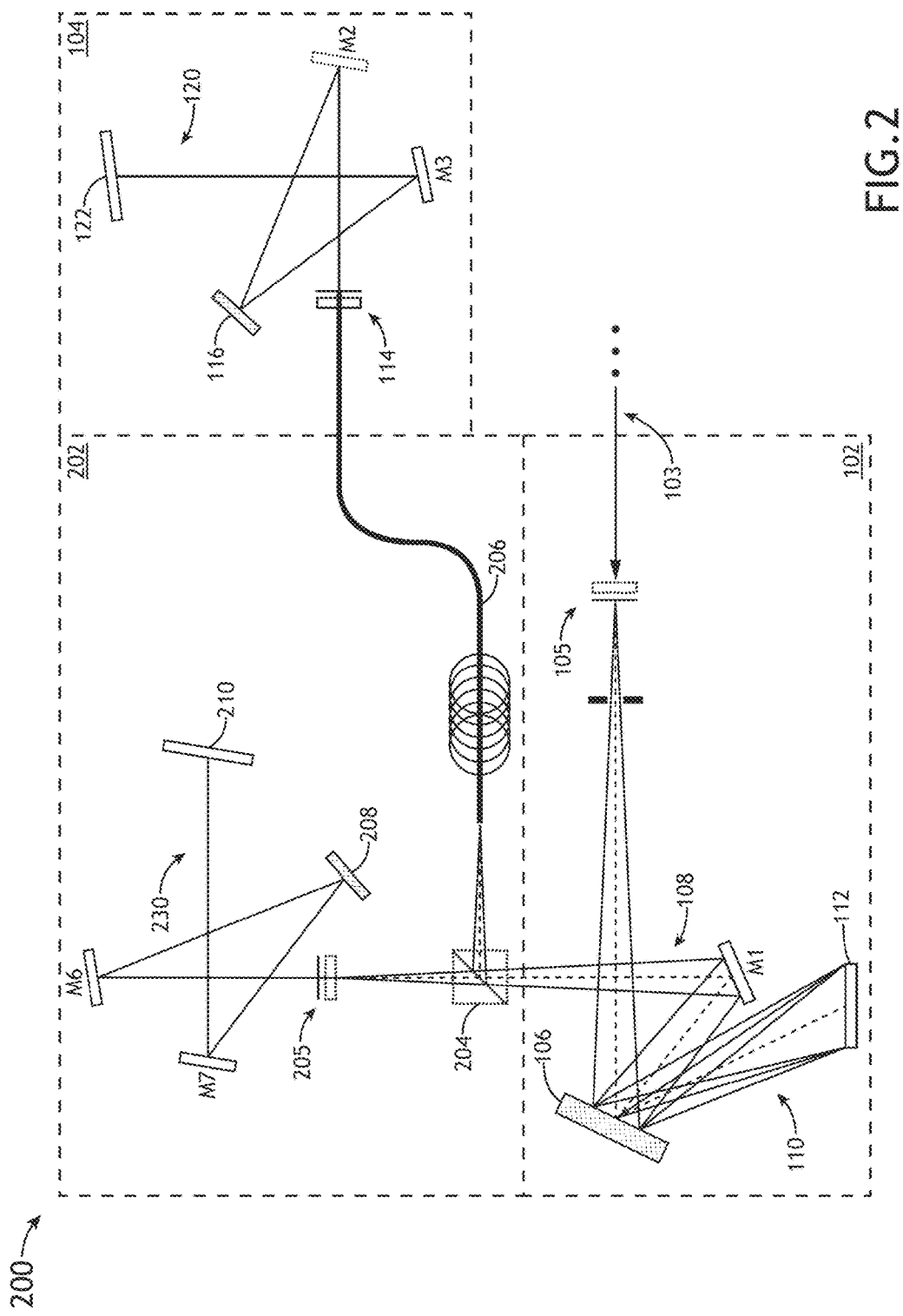
FIG. 2 illustrates a wideband spectrograph including three cascaded spectrograph assemblies, in accordance with one or more embodiments of the present disclosure.

FIG. 2 illustrates a wideband spectrograph 200 including three cascaded spectrograph assemblies, in accordance with one or more additional and/or alternative embodiments of the present disclosure.

It is noted that the various embodiments and configurations discussed previously herein with respect to spectrograph assemblies 102 and 104 found in FIG. 1A and FIG. 1B should be interpreted to extend to FIG. 2 unless otherwise noted.

In one embodiment, the wideband spectrograph includes a third spectrograph assembly 202 configured for detecting illumination in a third wavelength range. In another embodiment, the third spectrograph assembly 202 is different from the wavelength ranges detected by the first spectrograph assembly 102 and the second spectrograph assembly 104 to allow for simultaneous measurement of multiple spectral ranges across an even more extended overall spectral range relative to the example in FIG. 1A.

In one embodiment, the third spectrograph assembly 202 is optically coupled to the first spectrograph assembly 102. In this embodiment, the first cascading beam 108 is directed from the first dispersion element 106 of the first spectrograph assembly 102 to a beam splitter 204. The beam splitter 204 separates the first cascading beam 108 into a first beam component directed to slit 114 of the second spectrograph assembly 104 and a second beam component directed to slit 205 of the third spectrograph assembly 202. In another embodiment, the first beam component is directed to slit 114 of the second spectrograph assembly via a fiber optic cable 206. In another embodiment, at least a portion of the second beam component propagates through slit 205 to a sixth mirror M6. In another embodiment, the sixth mirror M6 directs the second beam component to a third dispersion element 208.

In another embodiment, the third dispersion element 208 separates a third sampling beam 230 from the second beam component (from the second spectrograph assembly). In another embodiment, the third sampling beam 230 is formed by one or more portions of diffracted light from the third dispersion element 208. In another embodiment, the third detector 210 is positioned so as to receive the third sampling beam 230 from the third dispersion element 208. For example, the third spectrograph assembly 202 may include mirror M7, which is arranged to receive diffracted light from the third dispersion element 208 and direct it to the third detector 210.

The one or more third dispersion elements 208 may include any dispersion element known in the art, such as, but not limited to, a grating structure. For example, a third dispersion element 208 may include, but is not limited to, a diffraction grating.

The third detector 210 may include any light detector device known in the art capable of detecting illumination within the third wavelength range. For example, the third detector 208 may include a light detector capable of detecting light within the spectral range of 900 to 2500 nm. For instance, the third detector 208 may include, but is not limited to, one or more InGaAs-based CCD detectors.

In another embodiment, the third spectrograph assembly 202 is purged with a selected purge gas (e.g., argon, nitrogen, and the like). In another embodiment, the third spectrograph assembly 202 is maintained in air.

It is noted that the use of the first, second and third spectrograph assemblies provides simultaneous measurement of three spectral ranges (e.g., 115-300 nm, 250-1100 nm and 900-2500 nm) to provide very wideband spectrographic capabilities. In addition, the implementation of the three spectrograph assemblies 102, 104 and 202 provides that four octaves of wavelength dynamic range may be realized.

Figure 3:
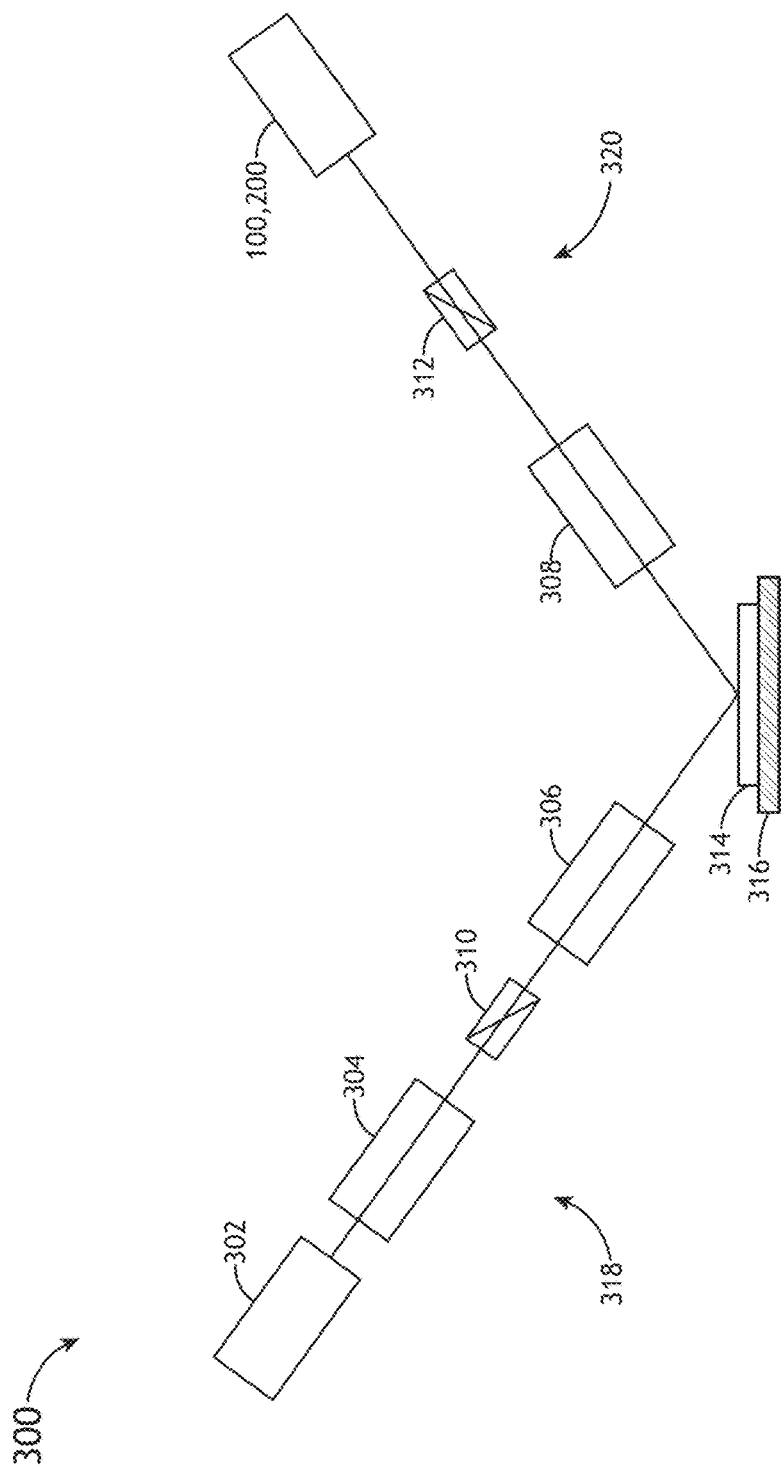
FIG. 3 illustrates a metrology system incorporating a wideband spectrograph, in accordance with one or more embodiments of the present disclosure.

FIG. 3 illustrates an optical characterization system 300 equipped with one or more wideband spectrographs, in accordance with one or more embodiments of the present disclosure.

The optical characterization system 300 may include a semiconductor processing tool requiring one or more spectroscopic sensors to perform metrology on a given semiconductor sample. It is noted that the optical characterization system may incorporate the wideband spectrograph 100/200 discussed throughout the present disclosure. In this regard, wideband spectrograph 100, 200 of the present disclosure may be implemented within the optical characterization system 300 such that the spectrograph 100/200 receives light collected from a sample as the input beam 103 into the spectrograph.

In one embodiment, as depicted in FIG. 3, the optical characterization system 300 includes a spectroscopic metrology tool. In one embodiment, the spectroscopic metrology tool is a spectroscopic ellipsometer. For example, the system 300 may include, but is not limited to, a spectroscopic ellipsometer configured to perform measurements of thin film properties of a sample (e.g., semiconductor wafer), CD profile metrology and/or overlay pattern registration.

In this embodiment, the metrology tool 300 includes a broadband light source 302 for generating broad band illumination. For example, the broadband light source 302 may include, but is not limited to, laser produced plasma (LPP) broad band light source (e.g., CW excited LPP source or pulsed laser excited LPP source).

In another embodiment, the metrology tool 300 includes one or more source optics 304. The source optics 304 may include any broadband illumination source optics in the art used to collect broadband light from a source and direct the broadband light along the illumination path of the metrology tool 300 to sample 314 disposed on stage 316. For example, the source optics 304 may include, but are not limited to, one or more collection optics (e.g., collection mirrors), mirrors, lenses, collimators, homogenizers, and the like.

In another embodiment, the metrology tool 300 includes one or more focusing optics 306. The one or more focusing optics 306 may include any focusing optics known in the art used to focus light from a broadband light source onto the surface of a sample. For example, the one or more focusing optics 306 may include, but are not limited, one or more lenses, mirrors, and the like.

In another embodiment, the metrology tool 300 includes one or more collection optics 308. The one or more collection optics 308 may include any collection optics known in the art used to collect light emanating (e.g., reflected, diffracted, scattered, or emitted) from a sample (e.g., semiconductor wafer) and direct the light to the spectrograph 100/200. For example, the one or more collection optics 308 may include, but are not limited, one or more lenses, mirrors, and the like.

In another embodiment, the metrology tool 300 includes a polarizer 310 positioned in the illumination arm 318 and an analyzer 312 positioned in the collection arm 320.

It is noted that the optical characterization system 300 is not limited to the spectroscopic ellipsometer configuration described previously herein. Rather, the optical characterization 300 may incorporate the spectrograph 100/200 in the context of any optical configurations known in the art of sample characterization. For example, the optical characterization system 300 may be configured in any one of the following characterization configurations: a spectroscopic ellipsometer for thin film metrology; a spectroscopic ellipsometer with multiple angles of illumination; spectroscopic ellipsometer configured for measuring Mueller matrix elements (e.g., using rotating compensator(s)); a single-wavelength ellipsometer; angle-resolved ellipsometer for beam profiling, an angle-resolved reflectometer for beam profiling, a spectroscopic reflectometer, a single-wavelength reflectometer, an imaging system, a scatterometer for critical dimension analysis, a scatterometer for pattern overlay metrology, or a general purpose scatterometer.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A spectrograph apparatus comprising:
    a first spectrograph assembly, the first spectrograph assembly comprising:
        one or more first dispersion elements for separating an input beam into a sampling beam and a first cascading beam; and
        one or more first detectors arranged to receive the sampling beam from the one or more dispersion elements, wherein the one or more first detectors are configured to detect illumination within a first wavelength range;
    a second spectrograph assembly optically coupled to the first spectrograph assembly and configured to receive the first cascading beam from the one or more dispersion elements of the first spectrograph assembly, the second spectrograph assembly comprising:
        one or more second dispersion elements for separating the first cascading beam from the first spectrograph assembly into a second sampling beam and a second cascading beam; and
        one or more second detectors arranged to receive the second sampling beam from the one or more second dispersion elements, wherein the one or more second detectors are configured to detect illumination within a second wavelength range different from the first wavelength range; and
    a third spectrograph assembly optically coupled to the second spectrograph assembly and configured to receive the second cascading beam from the one or more second dispersion elements of the second spectrograph assembly, the third spectrograph assembly comprising:
        one or more third dispersion elements for separating the second cascading beam from the second spectrograph assembly into a third sampling beam; and
        one or more third detectors arranged to receive the third sampling beam from the one or more third dispersion elements, wherein the one or more third detectors are configured to detect illumination within a third wavelength range different from the first wavelength range and the second wavelength range, wherein the third wavelength range comprises a wavelength range of 900 to 2500 nm.

2. The apparatus of claim 1, wherein the first cascading beam corresponds to the $0^{th}$ order beam from the separation of the input beam by the one or more first dispersion elements.

3. The apparatus of claim 1, wherein the second cascading beam corresponds to the $0^{th}$ order beam from the separation of the first cascading beam by the one or more second dispersion elements.

4. The apparatus of claim 1, wherein at least one of the first dispersion elements or the second dispersion elements comprise:
    one or more grating structures.

5. The apparatus of claim 4, wherein the one or more grating structures comprise:
    one or more diffraction gratings.

6. The apparatus of claim 1, wherein at least one of the first detector or the second detector comprise:
    one or more silicon-based charged coupled devices.

7. The apparatus of claim 1, wherein the first wavelength range comprises 115 to 300 nm.

8. The apparatus of claim 1, wherein the first wavelength range comprises 250 to 1100 nm.

9. The apparatus of claim 1, wherein the first spectrograph assembly is purged with a selected purge gas.

10. The apparatus of claim 1, wherein the first spectrograph assembly is maintained in vacuum.

11. The apparatus of claim 1, wherein the second spectrograph assembly is purged with a selected purge gas.

12. The apparatus of claim 1, wherein the second spectrograph assembly is maintained in air.

13. The apparatus of claim 1, wherein the one or more third dispersion elements comprise:
    one or more grating structures.

14. The apparatus of claim 13, wherein the one or more grating structures comprise:
    one or more diffraction gratings.

15. The apparatus of claim 13, wherein the third spectrograph assembly is purged with a selected purge gas.

16. The apparatus of claim 13, wherein the third spectrograph assembly is maintained in air.

17. The apparatus of claim 1, wherein the third detector comprises:
one or more InGaAs-based charged coupled devices.

18. A spectrograph apparatus comprising:
a first spectrograph assembly, the first spectrograph assembly comprising:
one or more first dispersion elements for separating an input beam into a sampling beam and a cascading beam; and
one or more first detectors arranged to receive the sampling beam from one or more grating structures, wherein the one or more first detectors are configured to detect illumination within a first wavelength range;
a beam splitter positioned within the cascading beam so as to split the cascading beam into a first component and a second component;
a second spectrograph assembly optically coupled to the first spectrograph assembly via the beam splitter and configured to receive the first component of the cascading beam from the one or more dispersion elements of the first spectrograph assembly, the second spectrograph assembly comprising:
one or more second dispersion elements for forming a second sampling beam; and
one or more second detectors arranged to receive the second sampling beam from the one or more second dispersion elements, wherein the one or more second detectors are configured to detect illumination within a second wavelength range different from the first wavelength range; and
a third spectrograph assembly optically coupled to the first spectrograph assembly via the beam splitter and configured to receive the second component of the cascading beam from the one or more dispersion elements of the first spectrograph assembly, the third spectrograph assembly comprising:
one or more third dispersion elements for forming a third sampling beam; and
one or more third detectors arranged to receive the third sampling beam from the one or more third dispersion elements, wherein the one or more third detectors are configured to detect illumination within a third wavelength range different from the first wavelength range and the second wavelength range, wherein the third wavelength range comprises a wavelength range of 900 to 2500 nm.

19. The apparatus of claim 18, wherein the cascading beam corresponds to the $0^{th}$ order beam from the separation of the input beam by the one or more first dispersion elements.

20. The apparatus of claim 18, wherein at least one of the first dispersion elements, the second dispersion elements or the third dispersion elements comprise:
one or more grating structures.

21. The apparatus of claim 20, wherein the one or more grating structures comprise:
one or more diffraction gratings.

22. The apparatus of claim 18, wherein at least one of the first detector or the second detector comprise:
one or more silicon-based charged coupled devices.

23. The apparatus of claim 18, wherein the third detector comprises:
one or more InGaAs-based charged coupled devices.

24. The apparatus of claim 18, wherein the first wavelength range comprises 115 to 300 nm.

25. The apparatus of claim 18, wherein the second wavelength range comprises 250 to 1100 nm.

26. The apparatus of claim 18, wherein the first spectrograph assembly is purged with a selected purge gas.

27. The apparatus of claim 18, wherein the first spectrograph assembly is maintained in vacuum.

28. The apparatus of claim 18, wherein the second spectrograph assembly is purged with a selected purge gas.

29. The apparatus of claim 18, wherein the second spectrograph assembly is maintained in air.

30. The apparatus of claim 18, wherein the third spectrograph assembly is purged with a selected purge gas.

31. The apparatus of claim 18, wherein the third spectrograph assembly is maintained in air.

32. A spectrograph apparatus comprising:
a first spectrograph assembly;
a second spectrograph assembly optically coupled to the first spectrograph assembly and configured to receive a first cascading beam from one or more dispersion elements of the first spectrograph assembly, wherein the first spectrograph is configured for detecting illumination in a first wavelength range and the second spectrograph assembly is configured for detecting illumination in a second wavelength range different from the first wavelength range; and
a third spectrograph assembly optically coupled to the second spectrograph assembly and configured to receive a second cascading beam from one or more dispersion elements of the second spectrograph assembly, wherein the third spectrograph assembly is configured for detecting illumination in a third wavelength range different from the first wavelength and the second wavelength range, wherein the third wavelength range comprises a wavelength range of 900 to 2500 nm.

33. A metrology system comprising:
an illumination arm;
a collection arm; and
one or more spectrograph sub-systems, wherein the one or more spectrograph sub-systems comprise:
a first spectrograph assembly;
a second spectrograph assembly optically coupled to the first spectrograph assembly and configured to receive a first cascading beam from one or more dispersion elements of the first spectrograph assembly, wherein the first spectrograph is configured for detecting illumination in a first wavelength range and the second spectrograph is configured for detecting illumination in a second wavelength range different from the first wavelength range; and
a third spectrograph assembly optically coupled to the second spectrograph assembly and configured to receive a second cascading beam from one or more dispersion elements of the second spectrograph assembly, wherein the third spectrograph assembly is configured for detecting illumination in a third wavelength range different from the first wavelength and the second wavelength range, wherein the third wavelength range comprises a wavelength range of 900 to 2500 nm.

* * * * *